US012760341B2

(12) United States Patent
Yee

(10) Patent No.: US 12,760,341 B2
(45) Date of Patent: Oct. 13, 2026

(54) ENZYMATIC TREATMENT OF FEEDSTOCK FOR HVO PRODUCTION

(71) Applicant: Novozymes A/S, Bagsvaerd (DK)

(72) Inventor: Hon Seng Yee, Kuala Lumpur (MY)

(73) Assignee: Novozymes A/S, Bagsvaerd (DK)

( * ) Notice: Subject to any disclaimer, the term of this patent is extended or adjusted under 35 U.S.C. 154(b) by 391 days.

(21) Appl. No.: 18/558,503

(22) PCT Filed: May 4, 2022

(86) PCT No.: PCT/EP2022/061890

§ 371 (c)(1),
(2) Date: Nov. 1, 2023

(87) PCT Pub. No.: WO2022/233897

PCT Pub. Date: Nov. 10, 2022

(65) Prior Publication Data

US 2024/0218404 A1 Jul. 4, 2024

(30) Foreign Application Priority Data

May 4, 2021 (MY) ............................ PI2021002457

(51) Int. Cl.
*C12N 9/20* (2006.01)
*C11C 1/04* (2006.01)
*C11C 1/08* (2006.01)
*C12N 9/88* (2006.01)
*C12P 7/6418* (2022.01)
*C12P 7/6436* (2022.01)

(52) U.S. Cl.
CPC ............ *C12P 7/6436* (2013.01); *C11C 1/045* (2013.01); *C11C 1/08* (2013.01); *C12N 9/20* (2013.01); *C12N 9/88* (2013.01); *C12P 7/6418* (2013.01); *C12Y 301/01032* (2013.01); *C12Y 301/01003* (2013.01); *C12Y 301/01004* (2013.01); *C12Y 301/04003* (2013.01); *C12Y 301/04011* (2013.01); *C12Y 406/01013* (2013.01)

(58) Field of Classification Search
CPC ............ C12P 7/6436; C12N 9/88; C12N 9/20
See application file for complete search history.

(56) References Cited

FOREIGN PATENT DOCUMENTS

| | | | |
|---|---|---|---|
| CN | 104629909 | A | 5/2005 |
| WO | 2005100579 | A1 | 10/2005 |

OTHER PUBLICATIONS

Cesarini et al., Biotechnology for Biofuels, 2014, 29, 7(1).
Roy et al., J. Am. Oil Chem. Soc., 2002, 845-846, 79(8).
Yang et al., J. Am. Oil Chem. Soc., 2008, 421-425, 85(5).

*Primary Examiner* — Tekchand Saidha
(74) *Attorney, Agent, or Firm* — Kelly Reynolds

(57) ABSTRACT

The present invention relates to methods of producing oil raw material for HVO production from vegetable oil which has been processed by an enzyme catalysed hydrolysis process and separation to reduce the content of phosphorous.

19 Claims, No Drawings

ENZYMATIC TREATMENT OF FEEDSTOCK FOR HVO PRODUCTION

CROSS-REFERENCE TO RELATED APPLICATIONS

This application is a 35 U.S.C. 371 national application of PCT/EP2022/061890, filed May 4, 2022, which claims priority or the benefit under 35 U.S.C. 119 from Malaysian Patent Application No. PI2021002457, filed May 4, 2021. The contents of these applications are fully incorporated herein by reference.

FIELD OF THE INVENTION

The present invention relates to the field of refining and/or producing HVO by the method of enzymatic treatment of vegetable oil to reduce the phosphorous content of the oil before the hydrotreatment process for production of HVO.

BACKGROUND ART

Hydrotreated Vegetable Oil (HVO) has become a well know renewable fuel known for the properties similar to fossil fuel and can be blended into fossil fuel. There are several associated problems to restrict its development, such as pre-processing of oil due to high contents of impurities like for instance phosphorous prior to the hydrotreatment process. The content of phosphorous has to be very low to protect the heterogenic catalyst used in the HVO process. Because of that, the pre-treatment of the vegetable oil material is very important to secure a very low phosphorous content.

In order to obtain a more economic production of HVO, there is a need for simpler and more efficient processes for purifying the vegetable oil raw materials to secure the low content of minerals especially phosphorous before the hydrotreatment process catalyzed by heterogenic catalysts.

SUMMARY OF THE INVENTION

An object of the present invention is to provide a method for the treatment of vegetable oil feedstock to efficiently reduce the phosphorous content.

The present invention relates to a method of producing oil raw material for HVO production having reduced phosphorus content from vegetable oil feedstock, said method comprising steps of: (a) mixing the vegetable oil feedstock with water; (b) hydrolyzing the vegetable oil feedstock mixture of step a) with a composition comprising a polypeptide having phospholipase activity and a polypeptide having lipase activity; (c) separating the light and heavy phase, and (d) subjecting the light phase to bleaching or distillation.

DETAILED DESCRIPTION OF THE INVENTION

Definitions

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms “a,” “an,” and “the” include plural referents unless the context clearly dictates otherwise. Thus, for example, reference to “a step” includes reference to one or more of such steps.

As used herein, “substantial” when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, “substantially free of” or the like refers to the lack of an identified element or agent in a composition. Particularly, elements that are identified as being “substantially free of” are either completely absent from the composition or are included only in amounts which are small enough so as to have no deleterious effect on the composition.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of about 1 percent to about 20 percent should be interpreted to include not only the explicitly recited concentration limits of 1 percent to about 20 percent, but also to include individual concentrations such as 2 percent, 3 percent, 4 percent, and sub-ranges such as 5 percent to 15 percent, 10 percent to 20 percent, etc.

Alkali: In the present context “alkali” refers interchangeably to a base that is soluble in water and forms hydroxide ions, such as NaOH, KOH, sodium carbonate, $Ca(OH)_2$, and $Mg(OH)_2$ and to the solution of a base in water.

Bleaching: The term “bleaching” refers to the process for removing minerals and color producing substances and for further purifying the fat or oil. Normally, bleaching is accomplished in an oil refining process.

HVO: HVO is hydrotreated vegetable oil which is a process catalyzed by inorganic heterogenic catalyst at high temperature and pressure and reacting hydrogen with the oil components to produce alkanes.

Chemical refining: In the present application, the term “chemical refining” is used synonymously with “alkali refining” and “alkaline refining”; the term also covering “caustic refining” and “caustic neutralization”.

Crude oil: The term “crude oil” refers to a pressed or extracted unrefined and unprocessed oil from a vegetable source, including but not limited to acai oil, almond oil, babassu oil, blackcurrant seed oil, borage seed oil, canola oil, cashew oil, castor oil, coconut oil, coriander oil, corn oil, cottonseed oil, crambe oil, flax seed oil, grape seed oil, hazelnut oil, hempseed oil, jatropha oil, jojoba oil, linseed oil, macadamia nut oil, mango kernel oil, meadowfoam oil, mustard oil, neat’s foot oil, olive oil, palm oil, palm kernel oil, palm olein, peanut oil, pecan oil, pine nut oil, pistachio oil, poppy seed oil, rapeseed oil, rice bran oil, safflower oil, sasanqua oil, sesame oil, shea butter, soybean oil, sunflower seed oil, tall oil, tsubaki oil walnut oil, varieties of “natural” oils having altered fatty acid compositions via Genetically Modified Organisms (GMO) or traditional “breading” such as high oleic, low linolenic, or low saturated oils (high oleic canola oil, low linolenic soybean oil or high stearic sunflower oils). The term also encompasses a mixture of several pressed or extracted unrefined and unprocessed oils from sources as defined above.

Soapstock and acid oil: Soapstock and acid oil is by products from processing vegetable oil. Soapstock is the result of neutralization of free fatty acids (FFA) in an oil with alkaline to saponify the FFA and separate it from the remaining oil phase. The soapstock is often neutralized with acid to recover the oil material including the FFA. This process produces acid oil.

Deodorization: "Deodorization" is a vacuum steam distillation process for the purpose of removing trace constituents that give rise to undesirable flavors, colors and odors in fats and oils. Normally this process is accomplished after refining and bleaching.

Degumming: Degumming refers to a process in which the phospholipid content of a phospholipid containing oil material is reduced. A typical enzymatic degumming process consist of a treatment step with acid, NaOH and enzyme followed by centrifugation to separate the hydrophobic and hydrophilic phases. After removal of non-hydratable phospholipids, hydratable phospholipids, and lecithins (known collectively as "gums") from the oil to produce a degummed oil or fat product that can be used for food production and/or non-food applications, e.g. biodiesel. In certain embodiments, the degummed oil has the phospholipids content of less than 200 ppm phosphorous, such as less than 150 ppm phosphorous, less than 100 ppm phosphorous, less than (or less than about) 50 ppm phosphorous, less than (or less than about) 40 ppm phosphorous, less than (or less than about) 30 ppm phosphorous, less than (or less than about) 20 ppm phosphorous, less than (or less than about) 15 ppm phosphorous, less than (or less than about) 10 ppm phosphorous, less than (or less than about) 7 ppm phosphorous, less than (or less than about) 5 ppm phosphorous, less than (or less than about) 3 ppm phosphorous or less than (or less than about) 1 ppm phosphorous.

Fatty acid alkyl esters (FAAE): Fatty acid alkyl esters are esters with a long carbon chain and an alkyl group, derived by transesterification fats with an alcohol. If the alcohol is methanol, the alkyl group in the fatty acid alkyl ester will be methyl, if the alcohol is ethanol, the alkyl group will be ethyl and so on.

Fatty acid feedstock: The term "fatty acid feedstock" or "vegetable oil feedstock" is defined herein as a substrate comprising triglyceride. In addition to triglyceride, the substrate may comprise diglyceride, monoglyceride, free fatty acid or any combination thereof. Any oils and fats of vegetable origin comprising fatty acids may be used as substrate for producing fatty acid alkyl esters in the process of the invention. The fatty acid feedstock may be oil selected from the group consisting of: algae oil, castor oil, coconut oil (copra oil), corn oil, cottonseed oil, flax oil, grape seed oil, hemp oil, jatropha oil, jojoba oil, mustard oil, canola oil, palm oil, palm stearin, palm olein, palm kernel oil, peanut oil, rapeseed oil, rice bran oil, safflower oil, soybean oil, sunflower oil, tall oil, and oil from halophytes, or any combination thereof. The fatty acid feedstock may be crude, refined, bleached, deodorized, degummed, or any combination thereof.

Fatty acid methyl esters (FAME): Fatty acid methyl esters are esters with a long carbon chain and a methyl group, derived by transesterification of fats with methanol.

Free fatty acids (FFA): A free fatty acid is a carboxylic acid with a long carbon chain. Most naturally occurring fatty acids have an unbranched chain of an even number of carbon atoms, from 4 to 28. Free fatty acids are usually derived from fats (triglycerides (TAG), diglycerides (DAG), monoglyceride(DAG)), phospholipids or lyso-phospholipids. Triglycerides are formed by combining glycerol with three fatty acid molecules. The hydroxyl (HO—) group of glycerol and the carboxyl (—COOH) group of the fatty acid join to form an ester. The glycerol molecule has three hydroxyl (HO—) groups. Each fatty acid has a carboxyl group (—COOH). Diglycerides are formed by combining glycerol with two fatty acid molecules. Monoglycerides are formed by combining glycerol with one fatty acid molecule.

Fractionation: Fractionation is the process of separating the triglycerides in fats and oils by difference in melt points, solubility or volatility. It is most commonly used to separate fats that are solid at room temperature but is also used to separate triglycerides found in liquid oils.

Gum: In the context of the present invention "gum", "gums" or "gum fraction" refers to a fraction enriched in phosphatides, which is separated from the bulk of vegetable oil during a degumming process. "Gums" consist mainly of phosphatides but also contain entrained oil, contain nitrogen and sugar and meal particles Heterologous: The term "heterologous" means, with respect to a host cell, that a polypeptide or nucleic acid is not naturally occurring in a host cell. The term "heterologous" means, with respect to a polypeptide or nucleic acid, that a control sequence, e.g., promoter, or domain of a polypeptide or nucleic acid is not naturally associated with the polypeptide or nucleic acid.

Host cell: The term "host cell" means any microbial or plant cell into which a nucleic acid construct or expression vector comprising a polynucleotide of the present invention has been introduced. Methods for introduction include but are not limited to protoplast fusion, transfection, transformation, electroporation, conjugation, and transduction. In some embodiments, the host cell is an isolated recombinant host cell that is partially or completely separated from at least one other component with, including but not limited to, for example, proteins, nucleic acids, cells, etc.

Hydrolysis: The term "hydrolysis" is an enzyme catalyzed process for production of free fatty acids from glycerides and/or phospholipids by reacting the oil components with $H_2O$ is called hydrolysis process or fat-splitting. The enzyme used in hydrolysis process to react with lipase and phospholipase are called lipase and phospholipase, respectively.

Isolated: The term "isolated" means a polypeptide, nucleic acid, cell, or other specified material or component that is separated from at least one other material or component with which it is naturally associated as found in nature, including but not limited to, for example, other proteins, nucleic acids, cells, etc. An isolated polypeptide includes, but is not limited to, a culture brother containing the secreted polypeptide.

Variant: The term "variant" means a polypeptide having phospholipase C activity comprising an alteration, i.e., a substitution, insertion, and/or deletion, at one or more (e.g., several) positions. As used herein, "reaction" is intended to cover single step and multi-step reactions which can be direct reactions of reactants to products or may include one or more intermediate species which can be either stable or transient.

A substitution means replacement of the amino acid occupying a position with a different amino acid; a deletion means removal of the amino acid occupying a position; and an insertion means adding an amino acid adjacent to and immediately following the amino acid occupying a position.

Lipolytic Enzyme

The one or more lipolytic enzyme applied in the method of the present invention is selected from lipases, phospholipases, cutinases, acyltransferases or a mixture of one and more of lipase, phospholipase, cutinase and acyltransferase. The one or more lipolytic enzyme is selected from the enzymes in EC 3.1.1, EC 3.1.4, and EC 2.3. The one or more lipolytic enzyme may also be a mixture of one or more lipases. The one or more lipolytic enzyme may include a lipase and a phospholipase. The one or more lipolytic enzyme includes a lipase of EC 3.1.1.3. The one or more lipolytic enzyme includes a lipase having activity on tri-, di-, and monoglycerides.

Lipases: A suitable lipolytic enzyme may be a polypeptide having lipase activity, e.g., one selected from the *Candida antarctica* lipase A (CALA) as disclosed in WO 88/02775, the *C. antarctica* lipase B (CALB) as disclosed in WO 88/02775 and shown in SEQ ID NO:1 of WO2008065060, the *Thermomyces lanuginosus* (previously *Humicola lanuginosus*) lipase disclosed in EP 258 068), the *Thermomyces lanuginosus* variants disclosed in WO 2000/60063 or WO 1995/22615, in particular the lipase shown in positions 1-269 of SEQ ID NO: 2 of WO 95/22615, the *Hyphozyma* sp. lipase (WO 98/018912), and the *Rhizomucor miehei* lipase (SEQ ID NO:5 in WO 2004/099400), a lipase from *P. alcaligenes* or *P. pseudoalcaligenes* (EP 218 272), *P. cepacia* (EP 331 376), *P. glumae, P. stutzeri* (GB 1,372,034), *P. fluorescens, Pseudomonas* sp. strain SD 705 (WO 95/06720 and WO 96/27002), *P. wisconsinensis* (WO 96/12012); a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422). Also preferred is a lipase from any of the following organisms: *Fusarium oxysporum, Absidia reflexa, Absidia corymbefera, Rhizomucor miehei, Rhizopus delemar* (*oryzae*), *Aspergillus niger, Aspergillus tubingensis, Fusarium heterosporum, Aspergillus oryzae, Penicilium camembertii, Aspergillus foetidus, Aspergillus niger, Aspergillus oryzae* and *Thermomyces lanuginosus*, such as a lipase selected from any of SEQ ID NOs: 1 to 15 in WO 2004/099400.

A lipase which is useful in relation to the present invention is a lipase having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or even 100% sequence identity to the polypeptide shown in positions 1-269 of SEQ ID NO: 2 of WO 95/22615 or to the polypeptide shown in SEQ ID NO:1 of WO2008/065060.

Commercial lipase preparations suitable for use in the process of the invention include LIPOZYME CALB L, LIPOZYME® TL 100L, CALLERA™ TRANS and Eversa® Transform (all available from Novozymes A/S).

Lipase Activity:

In the context of the present invention, the lipolytic activity may be determined as lipase units (LU), using tributyrate as substrate. The method is based on the hydrolysis of tributyrin by the enzyme, and the alkali consumption to keep pH constant during hydrolysis is registered as a function of time

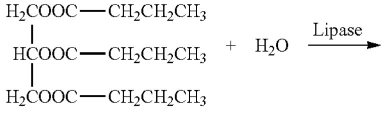

(tributyrin)

-continued

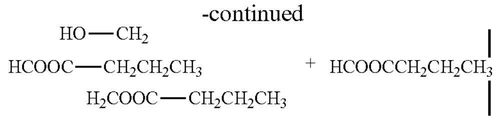

(butyric acid)

According to the invention, one lipase unit (LU) may be defined as the amount of enzyme which, under standard conditions (i.e. at 30° C.; pH 7.0; with 0.1% (w/v) Gum Arabic as emulsifier and 0.16 M tributyrine as substrate) liberates 1 micromol titrable butyric acid per minute. Alternatively, lipolytic activity may be determined as Long Chain Lipase Units (LCLU) using substrate pNP-Palmitate (C:16) when incubated at pH 8.0, 30° C., the lipase hydrolyzes the ester bond and releases pNP, which is yellow and can be detected at 405 nm.

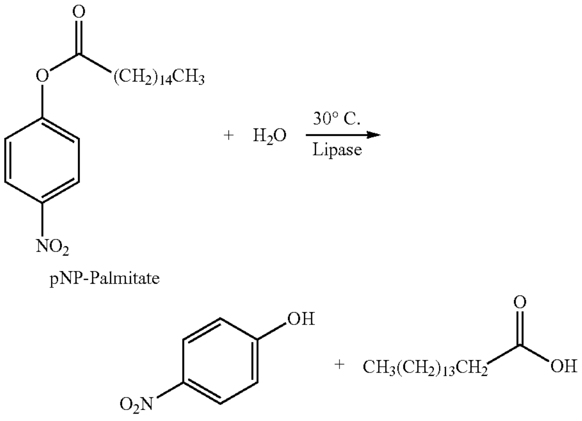

pNP-Palmitate 405 nm pNP

Phospholipases:

The one or more lipolytic enzyme may include a polypeptide having phospholipase activity, preferably phospholipase A1, phospholipase A2, phospholipase B, phospholipase C, phospholipase D, lyso-phospholipases activity, and/or any combination thereof. In the process of the invention the one or more lipolytic enzyme may be a phospholipase, e.g., a single phospholipase such as A1, A2, B, C, or D; two or more phospholipases, e.g., two phospholipases, including, without limitation, both type A and B; both type A1 and A2; both type A1 and B; both type A2 and B; both type A1 and C; both type A2 and C; or two or more different phospholipases of the same type.

The one or more lipolytic enzyme may be a polypeptide having phospholipase activity, as well as having acyltransferase activity, e.g., a polypeptide selected from the polypeptides disclosed in WO 2003/100044, WO 2004/064537, WO 2005/066347, WO 2008/019069, WO 2009/002480, and WO 2009/081094. Acyltransferase activity may be e.g., determined by the assays described in WO 2004/064537.

The phospholipase may be selected from the polypeptides disclosed in WO 2008/036863 and WO 20003/2758. Suitable phospholipase preparations are PURIFINE® (available from Verenium) and LECITASE® ULTRA (available from Novozymes A/S). An enzyme having acyltransferase activity is available as the commercial enzyme preparation LYSOMAX® OIL (available from Danisco A/S).

Phospholipases: The term "phospholipase" is defined herein as a phospholipolytic (EC number 3.1.1.4) enzyme that converts phospholipids into fatty acids and other lipophilic substances. For example, phospholipases as disclosed in WO 2018/171552

Phospholipase A activity: In the context of the present invention the term "phospholipase A activity" comprises enzymes having phospholipase A1 and/or phospholipase A2 activity (A1 or A2, EC 3.1.1.32 or EC 3.1.1.4), i.e., hydrolytic activity towards one or both carboxylic ester bonds in phospholipids such as lecithin. A phospholipase having both A1 and A2 activity is also referred to as a phospholipase B.

For purposes of the present invention, phospholipase A activity is preferably determined according to the following procedure:

Phospholipase A Activity (LEU)

In the LEU assay, the phospholipase A activity is determined from the ability to hydrolyze lecithin at pH 8.0, 40° C. The hydrolysis reaction can be followed by titration with NaOH for a reaction time of 2 minutes. The phospholipase from *Fusarium oxysporum* (LIPOPAN F) disclosed in WO 1998/26057 has an activity of 1540 LEU/mg enzyme protein and may be used as a standard.

Plate Assay

A) Buffers is a mixture of 100 mM HEPES and 100 mM Citrate with pH adjusted from pH 3.0 to pH 7.0.

B) 2% Agarose (Litex HSA 1000) is prepared by mixing and cooking in buffers (A)) for 5 minutes followed by cooling to approximately 60° C.

C) Substrate is L-alfa Phosphatidylcholine, 95% from Soy (Avanti 441601) dispersed in water (MilliQ) at 60° C. for 1 minute with Ultra Turrax.

D) Purified enzyme solutions of LECITASE ULTRA and the mature phospholipase of SEQ ID NO: 2 were diluted to 0.4 mg/ml.

Plates are casted by mixing of 5 ml substrate (C)) and 5 ml Agarose (B)) gently mixed into petri dishes with diameter of 7 cm and cooled to room temperature before holes with a diameter of approximately 3 mm are punched by vacuum. Ten microliters diluted enzyme (D)) is added into each well before plates are sealed by parafilm and placed in an incubator at 55° C. for 48 hours. Plates are taken out for photography at regular intervals.

Phospholipase activity: In the context of the present invention, the term "phospholipase activity" refers to the catalysis of the hydrolysis of a glycerophospholipid or glycerol-based phospholipid.

Conditions facilitating hydrolysis of phospholipids: Selecting the conditions which will facilitate hydrolysis of phospholipids by phospholipid degrading enzymes is within the skill of a person skilled in the art, and includes for example adjusting pH, and/or temperature at which phospholipid degrading enzyme are active.

Phospholipase C activity: The term "phospholipase C activity" or "PLC activity" relates to an enzymatic activity that removes the phosphate ester moiety from a phospholipid to produce a 1,2 diacylglycerol. Most PLC enzymes belong to the family of hydrolases and phosphodiesterases and are generally classified as EC 3.1.4.3, E.C. 3.1.4.11 or EC 4.6.1.13. Phospholipase C activity may be determined according to the procedure described in the following Phospholipase C assay:

Phospholipase C activity assay: Reaction mixtures comprising 10 microL of a 100 mM p-nitrophenyl phosphoryl choline (p-NPPC) solution in 100 mM Borax-HCl buffer, pH 7.5 and 90 microL of the enzyme solution are mixed in a microtiter plate well at ambient temperature. The microtiter plate is then placed in a microtiter plate reader and the released p-nitrophenol is quantified by measurement of absorbance at 410 nm. Measurements are recorded during 30 min at 1 minute intervals. Calibration curves in the range 0.01-1 microL/ml p-nitrophenol are prepared by diluting a 10 micromol/ml p-nitrophenol stock solution from Sigma in Borax-HCl buffer. One unit will liberate 1.0 micromol/minute of p-NPPC at ambient temperature.

Phospholipase C specificity: The term "phospholipase C specificity" relate to a polypeptide having phospholipase C activity where the activity is specified towards one or more phospholipids, with the four most important once being phosphatidylcholine (PC), phosphatidylethanolamine (PE), phosphatidic acid (PA) and phosphatidyl inositol (PI). Phospholipase C specificity may be determined by $^{31}$P-NMR as described above in relation to the term "phospholipase activity".

PC and PE-specific phospholipase C: The terms "PC and PE-specific phospholipase C" and "phospholipase C having specificity for phosphatidyl choline (PC) and phosphatidyl ethanolamine (PE)" and "polypeptide having activity towards phosphatidylcholine (PC) and phosphatidylethanolamine (PE)" are used interchangeably. They relate to a polypeptide having activity towards phosphatidylcholine (PC), phosphatidylethanolamine (PE). In addition to the PC and PE specificity it may also have some activity towards phosphatidic acid (PA) and phosphatidyl inositol (PI). Preferably a PC and PE specific phospholipase C removes at least 30%, 40%, 50%, 60%, 70% or 80%, even more preferred it removes 90% and most preferred it removes between 90% and 100% of the PC in the oil or fat and 40%, 50%, 60%, 70% or 80%, even more preferred it removes 90% and most preferred it removes between 90% and 100% of the PE in the oil or fat.

PI-Specific Phospholipase C: The terms "PI-specific phospholipase C", "Phosphatidylinositol phospholipase C" and "polypeptide having activity towards phosphatidylinositol (PI)" are used interchangeably. They relate to a polypeptide having activity towards phosphatidyl inositol (PI), meaning that its activity towards phosphatidylcholine (PC), phosphatidylethanolamine (PE), phosphatidic acid (PA) is low compared to the PI activity. PI-specific phospholipase C enzymes can either belong to the family of hydrolases and phosphodiesterases classified as EC 3.1.4.11 or to the family of lyases classified as EC 4.6.1.13. Preferably a PI-specific phospholipase C removes at least 30%, 40%, 50%, 60%, 70% or 80%, even more preferred it removes 90% and most preferred it removes between 90% and 100% of the PI in the oil or fat.

Preferably a PI-specific Phospholipase C removes at least 20% more PI when compared to the amount of PC, PE or PA it can remove, more preferred at least 30%, 40%, even more preferred at least 50% and most preferred at least 60% more PI when compared to the amount of PC, PE or PA it can remove.

PC-, PE-, PA- and PI-Specific Phospholipase C: The terms "PC-, PE-, PA,- and PI-specific phospholipase C", and "polypeptide having activity towards phosphatidylcholine (PC), phosphatidylethanoamine (PE), phosphatidic acid (PA) and phosphatidylinositol (PI)" are used interchangeably. They relate to a polypeptide having activity towards phosphatidylcholine (PC), phosphatidylethanoamine (PE), phosphatidic acid (PA), and phosphatidyl inositol (PI). Preferably a PC-, PE-, PA,- and PI-specific phospholipase C removes at least 30%, 40%, 50%, 60%, 70% or 80%, even more preferred it removes 90% and most preferred it removes between 90% and 100% of the PC in the oil or fat and 40%, 50%, 60%, 70% or 80%, even more preferred it removes 90% and most preferred it removes between 90% and 100% of the PE in the oil or fat.

Cutinases: The one or more lipolytic enzyme may include a polypeptide having cutinase activity.

The cutinase may e.g., be selected from the polypeptides disclosed in WO 2001/92502, in particular the *Humicola insolens* cutinase variants disclosed in Example 2.

Preferably, the one or more lipolytic enzyme is an enzyme having at least 60%, at least 70%, at least 80%, at least 90%, at least 95%, at least 96%, at least 97%, at least 98%, or even at least 99% identity to any of the aforementioned lipases, phospholipases, cutinases, and acyltransferases.

In one embodiment, the one or more lipolytic enzyme has at least 60%, at least 70%, at least 80%, at least 90%, at least 95%, at least 96%, at least 97%, at least 98%, at least or even at least 99% identity to the amino acid sequence shown as positions 1-269 of SEQ ID NO: 2 of WO 95/22615.

Enzyme sources and formulation: The one or more lipolytic enzyme used in the process of the invention may be derived or obtainable from any of the sources mentioned herein. The term "derived" means in this context that the enzyme may have been isolated from an organism where it is present natively, i.e. the identity of the amino acid sequence of the enzyme are identical to a native enzyme. The term "derived" also means that the enzymes may have been produced recombinantly in a host organism, the recombinant produced enzyme having either an identity identical to a native enzyme or having a modified amino acid sequence, e.g., having one or more amino acids which are deleted, inserted and/or substituted, i.e. a recombinantly produced enzyme which is a mutant and/or a fragment of a native amino acid sequence. Within the meaning of a native enzyme are included natural variants. Furthermore, the term "derived" includes enzymes produced synthetically by e.g., peptide synthesis. The term "derived" also encompasses enzymes which have been modified e.g., by glycosylation, phosphorylation etc., whether in vivo or in vitro. The term "obtainable" in this context means that the enzyme has an amino acid sequence identical to a native enzyme. The term encompasses an enzyme that has been isolated from an organism where it is present natively, or one in which it has been expressed recombinantly in the same type of organism or another, or enzymes produced synthetically by e.g., peptide synthesis. With respect to recombinantly produced enzyme the terms "obtainable" and "derived" refers to the identity of the enzyme and not the identity of the host organism in which it is produced recombinantly.

Accordingly, the one or more lipolytic enzyme may be obtained from a microorganism by use of any suitable technique. For instance, an enzyme preparation may be obtained by fermentation of a suitable microorganism and subsequent isolation of an enzyme preparation from the resulting fermented broth or microorganism by methods known in the art. The enzyme may also be obtained by use of recombinant DNA techniques. Such method normally comprises cultivation of a host cell transformed with a recombinant DNA vector comprising a DNA sequence encoding the enzyme in question and the DNA sequence being operationally linked with an appropriate expression signal such that it is capable of expressing the enzyme in a culture medium under conditions permitting the expression of the enzyme and recovering the enzyme from the culture. The DNA sequence may also be incorporated into the genome of the host cell. The DNA sequence may be of genomic, cDNA or synthetic origin or any combinations of these, and may be isolated or synthesized in accordance with methods known in the art.

The one or more lipolytic enzyme may be applied in any suitable formulation, e.g., as lyophilised powder or in aqueous solution.

Sequence Identity

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the −nobrief option) is used as the percent identity and is calculated as follows:

$$(\text{Identical Residues} \times 100)/(\text{Length of Alignment} - \text{Total Number of Gaps in Alignment})$$

Further, the invention relates to a batch process and/or a continuous, staged process to produce fatty acid alkyl esters using a first and a second lipolytic enzyme as described above, wherein the alcohol is added continuously or stepwise, and wherein the enzymes are recycled or used only once. If the enzymes are in an aqueous phase, this phase can be separated from the fatty phase by a decanter, a settler or by centrifugation. In the continuously process the two phases, oil and aqueous, respectively, can be processed counter-currently. Kosugi, Y; Tanaka, H. and Tomizuka, (1990), Biotechnology and Bioengineering, vol 0.36, 617-622, describes a continuous, counter-current process to hydrolyse vegetable oil by immobilized lipase.

The present invention relates to a method of producing oil raw material for HVO production having reduced phosphorus content from vegetable oil feedstock. The present inventors have surprisingly found that when performing lipase-phospholipase-catalyzed hydrolysis of glycerides and phospholipids in vegetable oil feedstock, the lipase-phospholipase is able to catalyze a reaction so that production of high content of free fatty acid takes place which enables phosphorous reduction when the light phase is separated from the heavy phase. Moreover, the present inventors have observed that the combination of lipase and phospholipase catalyzed reaction for hydrolyzing oil raw materials for HVO production is efficient in phosphorous reduction. Such observations have not been made previously.

In one aspect, the present invention provides a method of producing oil raw material for HVO production having reduced phosphorus content from vegetable oil feedstock, said method comprising steps of: (a) mixing the vegetable oil feedstock with water; (b) hydrolyzing the vegetable oil feedstock mixture of step a) with a composition comprising a polypeptide having phospholipase activity and a polypeptide having a polypeptide having lipase activity; (c) separating the light and heavy phase, and (d) subjecting the light phase to bleaching or distillation.

The vegetable oil could be, or could be derived from algae oil, canola oil, coconut oil, castor oil, copra oil, corn oil, distiller's corn oils, corn oil free fatty acid distillate, cottonseed oil, flax oil, fish oil, grape seed oil, hemp oil, jatropha oil, jojoba oil, mustard oil, canola oil, palm oil, palm stearin, palm olein, palm kernel oil, peanut oil, rapeseed oil, rice bran oil, safflower oil, soybean oil, sunflower oil, tall oil, oil from halophytes, palm oil free fatty acid distillate, soy oil free fatty acid distillate, soap stock fatty acid material, yellow grease, and brown grease or any combination thereof.

In one aspect, "vegetable oil feedstock" refers to any material or composition comprising soaps as well saponifiable material, i.e. lipids capable of reacting to produce soaps (salts of fatty acids). Saponifiable material in the mixed lipid feedstock can include, without limitation, glycerides, e.g. mono-glycerides, di-glycerides, or triglycerides, or a combination thereof, and/or phospholipids. In another aspect, the vegetable oil feedstock is a soapstock. In another aspect, the vegetable oil feedstock comprises soaps and saponifiable lipids e.g. glycerides and/or phospholipids. In another aspect, the vegetable oil feedstock is a mixture of soapstocks, comprising soaps, saponifiable material, e.g. glycerides and/or phospholipids, obtained during the processing of a natural oil. In another aspect, the vegetable oil feedstock is a soapstock washwater obtained from the processing of a crude natural oil following the neutralization step in the chemical refining process in such embodiments, the wash water can comprise water and soapstock, wherein the soapstock comprises soaps, glycerides, phospholipids, free fatty acids, and unsaponifiable material e.g. waxes and/or sterols.

The vegetable oil may be crude, refined, bleached, deodorized, degummed, or any combination thereof. The vegetable oil may be an intermediate product, a waste product or a by-product of oil or fat refining selected from the group consisting of: soap stock; acid oil; fatty acid distillates such as PFAD, soy fatty acid distillate, rapeseed fatty acid distillate, rice bran fatty acid distillate, etc.; gums from degumming; by-products from the production of omega-3 fatty acids derivates from fish oil; fat trap grease; yellow grease, and brown grease, free fatty acids like oleic acid; or fractions of oil obtained by physical separations; or any combinations thereof.

The method according to the invention may comprise contacting the vegetable oil with one or more chelation agents capable of complexing Ca and/or Mg ions prior to contacting it with the one or more phospholipid degrading enzymes.

Thus, one embodiment relates to the method of the invention, further comprising a step of chelation, said chelation comprising contacting the vegetable oil comprising phospholipids of step a. with one or more chelation agents capable of complexing Ca and/or Mg ions, prior to step b of contacting said vegetable oil with enzyme composition comprising lipase and phospholipase.

In one embodiment, said chelation agent is selected from the group consisting of one or more weak organic acids, such as citric acid and/or lactic acid.

In one embodiment, said chelation agent is phosphoric acid.

In one particular embodiment, the chelation agent comprises or consists of citric acid.

The selection of the amount of chelation agent is within the skill of the person skilled in the art. Chelation may be added in amount of for example 50 ppm to 5000 ppm, such as 100 ppm to 5000 ppm, for example 100 to 1500 ppm.

In a further embodiment, the chelation agent comprises or consists of ethylenediaminetetraacetic acid (EDTA).

In one aspect, the vegetable oil mixture comprises at most a water content in the range of 0.5-80% (w/w), such as in the range of 1-70% (w/w), in the range of 1-65% (w/w) or such as in the range of 10-60% (w/w).

In one aspect, the pH of the vegetable oil mixture is in the range of 3.5-11.0, such as 3.6-10.0, such as 3.5-9.0 or such as 4.0-8.0.

The aim of the treating of the vegetable oil comprising phospholipids with lipase and phospholipase is to allow the lipase and phospholipases to hydrolyse the glycerides and phospholipids present in the vegetable oil. The conditions of the incubation may be selected by the person skilled in the art.

The lipase comprises hydrolyzing a triacylglycerol to a diacylglycerol and a free fatty acid, or, hydrolyzing a triacylglycerol to a monoacylglycerol and free fatty acids, or, hydrolyzing a diacylglycerol to a monoacylglycerol and free fatty acids, or, hydrolyzing a monoacylglycerol to a free fatty acid and a glycerol, or, comprises hydrolyzing a triacylglycerol (TAG), a diacylglycerol (DAG) or a monoacylglycerol (MAG). The polypeptide having phospholipase converts the non-hydratable phospholipid in the vegetable oil to a hydratable form For example, the pH, and the temperature at which the incubation is carried out, and the time for which the incubation is carried out can be selected to suit the lipase and phospholipase.

In some embodiments, the incubation is at carried out at a pH in the range of from 4.5 to 12.0.

In some embodiments, the incubation is at carried out at a temperature in the range from 25-95° C., or such as 40° C.-70° C., or such as 50° C.-70° C.

In some embodiments, the incubation is at carried out for a time in the range from 1 to 48 hours, such as 2 to 24 hours, such as 2 to 8 hours, such as 2 to 6 hours.

Likewise, the person skilled in the art may select the dosage of lipase and phospholipase.

In one embodiment, the said one or more lipase and phospholipase are dosed in a total amount corresponding to 0.05-30 mg enzyme protein.

In one embodiment, the step of separating the light phase containing the free fatty acid from heavy phase may be performed in any means suitable, for example by centrifugation or by clarification (settling). Separation is performed using gravity separation, a centrifuge, a separator, membranes, and any combinations thereof. Free fatty acid is present in an amount at least >50%, at least 55%, at least >60%, at least >65%, at least >70%, at least >75%, at least >80% at least >85% or at least >90% of the light phase after separation.

In one embodiment, the phosphorous in the light phase is reduced by at least >30%, at least >35%, at least >40%, at least >45%, at least >50%, at least >55%, at least >60%, at least >65%, >70%, at least >75%, at least >80%, at least >85% or at least >90% compared to the content in the oil material before the hydrolysis process.

The method according to the invention may comprise contacting the vegetable oil with one or more antioxidant agents prior or during to contacting it with the lipase and phospholipase.

In one embodiment, the light phase is further processed by distillation to reduce the phosphorous further before it is used for production of HVO.

In one aspect, the free fatty acid is recovered using a distillation. Recovery using distillation enables HVO production of renewable diesel and other biofuels in an economically advantageous manner which helps for improvement in production economy.

In one embodiment, the separated light phase is subjected to bleaching that are used conventional refining processes known to the person of skill in the art. The bleaching is a method for reducing the phosphorous content if the oil material before the processing to HVO.

The usual method of bleaching is by adsorption of the color producing substances on an adsorbent material. Acid-activated bleaching earth or clay, sometimes called bentonite, is the adsorbent material that has been used most extensively. This substance consists primarily of hydrated aluminium silicate. Anhydrous silica gel and activated carbon also are used as bleaching adsorbents to a limited extent.

In alternative embodiments, fatty acids and fatty acid derivatives recovered are used as feedstock for production of renewable/green diesel, including renewable diesel known as "HVO" (hydrotreated vegetable oil) and "HEFA" (hydroprocessed esters and fatty acids), and "Paraffinic Diesel Fuel from Hydrotreatment" using the European standard definition for EN 15940. The general process for producing renewable diesel involves catalysts that hydrogenate alkene moieties and decarboxylate and/or decarbonylate carboxylic acid moieties of fatty acids to generate alkane profiles similar to those in petroleum-based diesel.

In alternative embodiments, fatty acids and fatty acid derivatives produced using methods as provided herein are used for renewable diesel production processes, for example, including: Vegan, ECOFINING™, Hydroflex, NEXBTL, UPM BioVerno, etc.); and, the fatty acids produced using methods as provided herein can either be used as-is or are first be converted to glycerides via glycerolysis before entering the catalytic hydrogenation/decarboxylation/decarbonylation section of those processes.

Depending on the purity of the fatty acids recovered from processes as provided herein, some pretreatment, e.g. bleaching, of the fatty acids must occur prior to their catalytic upgrading to renewable diesel.

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

EXAMPLES

Example 1. Treating Acid Oil with Phospholipase

Acid oil obtained from soy refining with characteristics as shown in Table 1 was used in a trial to show the effect of phospholipase treatment using different enzymes:

TABLE 1

| Soy Acid Oil Components | |
|---|---|
| % FFA (as oleic) | 55.0 |
| Phosphorus/ppm | 3199 |
| Magnesium/ppm | 265 |
| Calcium/ppm | 123 |
| Iron/ppm | 11 |

Oil was processed with phospholipase (Lecitase Ultra, Novozymes) as shown in Table 2. The results clearly showed a small decrease in phosphorous content between the phospholipase treated sample (796 ppm) and the control (1003 ppm) after 4 hours incubation and separation plus washing step This corresponds to 21% reduction in P-content. By prolonging the incubation with enzyme to 16 hours the P content decreased to 615 ppm (39% reduction). There was a large decrease in the content of the other minerals both in the control and the enzyme treated samples. Analysis of minerals was carried out using ICP instrument. FFA measured by titration with KOH and re-calculated as content of C-18 oleic acid.

TABLE 2

Effect of a typical enzymatic degumming procedure on an oil

| Trial | Feed | T1-Control | T2 | T3 |
|---|---|---|---|---|
| Temperature for acid conditioning (° C.) | | 85 | 85 | |
| Citric Acid monohydrate (%) | | 0.2 | 0.2 | |
| High shear Mixing | | 24000 rpm, 30 sec | 24000 rpm, 30 sec | |
| Stirring (rpm)/Time (mins) | | 350/30 | 350/30 | |
| NaOH/ppm in 4N solution | | 500 | 500 | |
| High shear Mixing | | 24000 rpm, 30 sec | 24000 rpm, 30 sec | |
| Enzyme | | No enzyme | 0.1% Lecitase Ultra | |
| % total water | | 10 | 10 | |
| High shear Mixing | | 24000 rpm, 30 sec | 24000 rpm, 30 sec | |
| Temperature (° C.)/ Stirring (rpm) | | 55/225/4 | 55/225/4 | |
| Incubation time, hours | | 4 | 4 | 16 |
| Deactivation of Enzyme | | | | |
| Temp (° C.)/Time (mins)/Stirring (rpm) | | 85/30/350 | 85/30/350 | 85/30/350 |
| Centrifugation force/ Time (mins) | | 2000 g/5 | 2000 g/5 | 2000 g/5 |
| Hot water washing on light phase | | | | |
| Temperature (° C.) | | 85 | 85 | 85 |
| % Hot water washing on light phase | | 10 | 10 | 10 |
| High shear Mixing | | 24000 rpm, 30 sec | 24000 rpm, 30 sec | 24000 rpm, 30 sec |
| Centrifugation force/ Time (mins) | | 2000 g/5 | 2000 g/5 | 2000 g/5 |
| Analysis after wash step | | | | |
| % FFA (as oleic) | 55.0 | 57.6 | 57.4 | 57.0 |
| Phosphorus/ppm | 3199 | 1003 | 796 | 615 |
| Magnesium/ppm | 265 | 3 | 2 | 2 |
| Calcium/ppm | 123 | 7 | 3 | 0 |
| Iron/ppm | 11 | 3 | 2 | 2 |

Example 2. Treating Acid Oil with Lipase

Oil with lower initial P-content was used. It was processed with lipase (Eversa Transform 2.0, Novozymes) as shown in Table 3. The results showed a decrease in phosphorous content from 304 ppm to 175 ppm (42% reduction) by the hydrolysis and separation process. No decrease was seen for the other minerals. The data for FFA content versus reaction time show that the hydrolysis reaction has taken place.

TABLE 3

| Effect of a hydrolysis process on the oil | | |
|---|---|---|
| Trial | Feed | Enzyme treated |
| Acid oil/g | | 200 |
| NaOH/ppm in 4N solution to adjust pH to 5 | | 2500 |
| % H2O | | 50 |
| Temp (° C.)/Stirring (rpm) | | 55/750 |
| Enzyme | | 0.5% ET2.0 |
| Time, hours | | 24 |
| Analysis | | |
| % FFA (as oleic) | | |
| 0 hour | | 68.6 |
| 6 hour | | 77.6 |
| 24 hour | | 82.5 |
| ICP-OES | | |
| Phosphorus/ppm | 304 | 175 |
| Magnesium/ppm | 3 | 4 |
| Calcium/ppm | 2 | 12 |
| Iron/ppm | 3 | <1 |

Example 3. Treating Soapstock with Different Phospholipases

Soy soapstock was used in a trial with addition of different phospholipases, two PLA and one PLC as shown in Table 4. PLC phospholipase had a very high P-content after the process whereas the two PLA enzymes Lecitase Ultra and Quara Low P reduced the P-content to 737 ppm and 284 ppm, respectively.

TABLE 4

| Treating soapstock | | | |
|---|---|---|---|
| Trial plan | TA | TB | TC |
| Pre-treatment step | | | |
| Temp/Stirr ng speed/Time | 75 deg C./ 150 rpm/2 h | 75 deg C./ 150 rpm/2 h | 75 deg C./ 150 rpm/ 2h |
| Water (%) | 21% | 21% | 21% |
| Phosphoric acid (%) | 9% | 9% | 9% |
| Target pH | 5 | 5 | 5 |
| Enzymatic soap spliting | | | |
| Temp/Stirring speed/Time | 55 deg C./ 200 rpm/16 h | 55 deg C./ 200 rpm/16 h | 55 deg C./ 200 rpm/16 h |
| Enzyme | 0.1% Lecitase Ultra | 0.1% Quara LowP | 0.1% Quara Boost |
| Centrifuge | 2000 g, 5 mins | 2000 g, 5 mins | 2000 g, 5 mins |
| Washing step (multiple time) | | | |
| Water (%) each time | 10% | 10% | 10% |
| Total citric acid use | 3% | 3% | 3% |
| High shear mixing | 24,000 rpm, 30 sec | 24,000 rpm, 30 sec | 24,000 rpm, 30 sec |
| Temp/Stirring speed/Time | 85 deg C./ 350 rpm/15 m | 85 deg C./ 350 rpm/15 m | 85 deg C./ 350 rpm/15 m |
| Centrifuge | 2000 g, 5 mins | 2000 g, 5 mins | 2000 g, 5 mins |
| Analysis | | | |
| FFA (C18:1) | 68.5% | 64.5% | 56.9% |
| P mg/kg | 737 | 284 | 3712 |
| Mg mg/kg | 3 | 3 | 63 |
| Ca mg/kg | 3 | 2 | 17 |
| Fe mg/kg | 0 | 0 | 0 |

Example 4. Treating Soapstock with Lipase and Phospholipase

Soapstock with 3436 ppm P obtained from soy refining with characteristics shown in Table 5 was used in a trial to show the effect of lipase and phospholipase treatment.

TABLE 5

| Soapstock Components | |
|---|---|
| Water, % | 50.6 |
| Gum, % | 8.6 |
| Soap, % | 10.8 |
| Oil and others, % | 30.0 |

Soapstock was processed with lipase Eversa Transform 2.0, Novozymes and phospholipase Lecitase Ultra, Novozymes as shown in Table 6. pH was adjusted by $H_2SO_4$ to the pH 1.4 for control and 4.6 for the enzyme treatment. Results clearly showed a decrease in phosphorous content between the lipase and phospholipase treated sample (148 ppm) and the control (372 ppm) after 20 hours incubation and separation plus washing step. This corresponds to 60% reduction 10 in P-content. FFA increase from 48.0 to 90.4% showed a significant hydrolysis of the oil components.

TABLE 6

| Treating soapstock with lipase and phospholipase | | |
|---|---|---|
| Trial Plan | Control | Lipase + phospholipase treatment |
| Weight (g) | 100 | 200 |
| H2SO4 % (95-97%) | 6.0% | 4.0% |
| Temp/Time/Stir speed | 85° C./2h/ (150-200) rpm | 85° C./2 h/ (200-400) rpm |
| Cooldown (deg C.) | 85 | 55 |
| Enzyme | — | 0.2% Eversa Transform, 0.1% Lecitase Ultra |
| Temp/Time/Stir speed | — | 55° C./20 h/ (150-200) rpm |
| Centrifuge at 2000 g | — | 5 min |
| H2SO4 % (95-97%) | — | 1.5% |
| Temperature (deg C) | — | 85 |
| High Shear Mix | — | 30 sec |
| Hot water | — | 10% |
| High Shear Mix | — | 30 sec |
| Heating | — | 15 mins, 85 deg C. |
| Centrifuge at 2000 g | — | 5 min |
| Results | | |
| % FFA (as C18:1)-before water wash | 48.0 | 190.4 |
| Phosphorus/ppm | 372 | 148 |
| Calcium/ppm | 4 | 13 |
| Magnesium/ppm | 3 | <1 |

Example 5. Soapstock-pH Adjusted and Hydrolyzed with a Combination of Lipase and Phospholipase

| Trial plan | TD | Soy acid oil |
|---|---|---|
| Pre-treatment step | | |
| Temp/Stirring speed/Time | 85 deg C./100 rpm/4 h | |
| Water (%) | 50% | |
| Phosphoric acid (%) | 10% | |
| Target pH | 5 | |

-continued

| Trial plan | TD | Soy acid oil |
| --- | --- | --- |
| Enzymatic soap spliting | | |
| Temp/Shaking speed/Time | 55 deg C./200 rpm/16 h | |
| Enzyme | 0.2% Eversa Transfomr 2.0 | |
| | 0.1% Lecitase Ultra | |
| Centrifuge | 2000 g, 5 mins | |
| Washing step | | |
| Phosphoric acid | 8% | |
| High Shear Mixing | 24,000 rpm, 30 sec | |
| Water (%) | 10% | |
| High Shear Mixing | 24,000 rpm, 30 sec | |
| Temp/Stirring speed/Time | 85 deg C./200 rpm/2 h | |
| Centrifuge | 2000 g, 5 mins | |
| Analysis | | |
| FFA (C18:1) | 92.8% | 55.0% |
| Soap content/ppm | 350 | ND |
| P mg/kg | 344 | 3199 |
| Mg mg/kg | 3 | 265 |
| Ca mg/kg | 2 | 123 |
| Fe mg/kg | 3 | 11 |

As result of the hydrolysis process followed by separation the P-content was reduced from 3199 ppm to 344 ppm.

The invention claimed is:

1. A method of purifying oil from vegetable oil feedstock for hydrotreated vegetable oil (HVO) production, said method comprising steps of:

(a) mixing the vegetable oil feedstock with water;

(b) hydrolyzing the vegetable oil feedstock mixture of step a) with a composition comprising a polypeptide having phospholipase activity and a polypeptide having lipase activity;

(c) separating the light and heavy phase, wherein the free fatty acid of the light phase after separation is >50% and (d) subjecting the light phase to bleaching or distillation.

2. The method of claim 1, wherein the vegetable oil feedstock mixture comprises >20% water.

3. The method of claim 1, wherein the free fatty acid is >70% of the light phase after separation.

4. The method of claim 1, wherein the free fatty acid is >80% of the light phase after separation.

5. The method of claim 1, wherein the free fatty acid is >90% of the light phase after separation.

6. The method of claim 1, wherein step b) is carried out at temperature 25° C.-80° C.

7. The method of claim 1, wherein step b) is carried out at temperature 40° C.-70° C.

8. The method of claim 1, wherein step b) is carried out at temperature 50° C.-70° C.

9. The method of claim 1, wherein the phosphorous content in the vegetable oil feedstock is reduced by at least 30 percent, when compared to a control without the phospholipase.

10. The method of claim 1, wherein the phosphorous content in the vegetable oil feedstock is reduced by at least 50 percent, when compared to a control without the phospholipase.

11. The method of claim 1, wherein the phosphorous content in the vegetable oil feedstock is reduced by at least 80 percent, when compared to a control without the phospholipase.

12. The method of claim 1, wherein the phosphorous content in the vegetable oil feedstock is reduced by at least 90 percent, when compared to a control without the phospholipase.

13. The method of claim 1, wherein the vegetable oil feedstock is selected from the group consisting of rapeseed oil, corn oil, mustard oil, olive oil, palm oil, palm kernel oil, peanut oil, safflower oil, sesame oil, soybean oil, nut oil, cottonseed oil, crambe oil, coconut oil, meadowfoam oil, vernonia oil, canola oil, jatropha oil, jojoba oil, grape seed oil, sunflower oil, and mixtures thereof.

14. The method of claim 1, wherein separation is performed using gravity separation, a decanter, a centrifuge, a separator, membranes, or any combination thereof.

15. The method of claim 1, wherein antioxidant agent is added to the vegetable oil feedstock before or during step b).

16. The method of claim 1, wherein said polypeptide having a polypeptide having lipase activity is derived from any one of *Rhizomucor miehei, Pseudomonas* sp., *Rhizopus niveus, Mucor javanicus, Rhizopus oryzae, Aspergillus niger, Penicillium camembertii, Alcaligenes* sp., *Acromobacter* sp., *Burkholderia* sp., *Thermomyces lanuginosus, Chromobacterium viscosum, Candida antarctica* B, *Candida rugosa, Candida antarctica* A, papaya seeds and pancreatin.

17. The method of claim 1, wherein said polypeptide having phospholipase activity is/are selected from the group consisting of:

a. A phospholipase C having specificity for Phosphatidylinositol (PI), b. A phospholipase C having specificity for phosphatidyl choline (PC) and Phosphatidyl ethanolamine (PE), c. A phospholipase C having specificity for Phosphatidyl choline (PC), Phosphatidyl ethanolamine (PE) Phosphatidic acid (PA) and Phosphatidylinositol (PI), d. A combination of a phospholipase A and a phospholipase C, such as a phospholipase C as defined in a) or b), e. A combination of a phospholipase A and a lysophospholipase, f. A phospholipase A, g. A combination of a) and b)

h. and/or combinations thereof.

18. The method of claim 1, wherein the light phase is further processed by distillation to reduce the phosphorous further before it is used for production of HVO.

19. The method of claim 1, wherein the light phase is further processed by bleaching to reduce the phosphorous further before it is used for production of HVO.

* * * * *